(12) United States Patent
Glockner et al.

(10) Patent No.: US 6,410,307 B1
(45) Date of Patent: Jun. 25, 2002

(54) MEMBRANE MODULE FOR TESTING ACTIVE SUBSTANCES AT CELLS

(75) Inventors: Herma Glockner, Kleinwallstadt; Horst-Dieter Lemke, Obernburg; Friedrich Hauck, Grossheubach; Christoph Zimmerer, Amorbach; Rudi Wollbeck, Erlenbach, all of (DE)

(73) Assignee: Acordis Industrial Fibers GmbH, Wuppertal (DE)

( * ) Notice: Subject to any disclaimer, the term of this patent is extended or adjusted under 35 U.S.C. 154(b) by 0 days.

(21) Appl. No.: 09/936,264

(22) PCT Filed: Mar. 2, 2000

(86) PCT No.: PCT/EP00/01819

§ 371 (c)(1),
(2), (4) Date: Nov. 21, 2001

(87) PCT Pub. No.: WO00/53796

PCT Pub. Date: Sep. 14, 2000

(30) Foreign Application Priority Data

Mar. 9, 1999 (DE) .......................................... 199 10 539

(51) Int. Cl.[7] .............................................. C12M 1/34
(52) U.S. Cl. ............................... 435/287.1; 435/297.1; 435/297.4
(58) Field of Search ........................... 435/289.1, 297.1, 435/297.4, 287.1

(56) References Cited

U.S. PATENT DOCUMENTS

| 4,937,196 A | | 6/1990 | Wrasidlo et al. | |
|---|---|---|---|---|
| 5,290,700 A | * | 3/1994 | Binot et al. ............... | 435/297.4 |
| 5,516,691 A | | 5/1996 | Gerlach | |
| 5,622,857 A | * | 4/1997 | Goffe ...................... | 210/321.8 |
| 5,676,924 A | | 10/1997 | Lipsky et al. | |
| 5,712,154 A | * | 1/1998 | Mullon et al. ............ | 435/283.1 |
| 6,271,023 B1 | * | 8/2001 | Baurmeister et al. .. | 210/321.64 |

FOREIGN PATENT DOCUMENTS

| DE | 36 33 891 A1 | 4/1988 |
|---|---|---|
| DE | 199 10 540.5 | 3/1999 |
| DE | 198 10 901 | 6/1999 |
| EP | 0 180 165 | 5/1986 |
| EP | 0 363 262 | 4/1990 |
| WO | WO 94/25074 | 11/1994 |
| WO | WO 99/28438 | 6/1999 |

OTHER PUBLICATIONS

U.S. application No. 09/936,266, Co–pending.
H.J. Schmoll et al., "Compendium of Internal Oncology", Spring 1996.

(List continued on next page.)

Primary Examiner—David A. Redding
(74) Attorney, Agent, or Firm—Oliff & Berridge, PLC

(57) ABSTRACT

Membrane module for testing active substances in cells with an interior chamber (2) which is limited by a lid (3), a bottom (4), and a side wall (5) and a system of first capillary membranes (6) and a system of second capillary membranes (11) located therein and possibly additional systems of capillary membranes, whereby the capillary membranes in interior chamber (2) are arranged in at least one flat layer parallel to bottom (4) and in interior chamber (2) in the extracapillary space a cell culture chamber is formed around the capillary membranes, whereby the capillary membranes have a lumen that can be filled with a fluid, are passing with at least one of its ends through the side wall (5) of interior chamber (2) and are embedded at this end separated by systems in a casting material (9, 10) so that interior chamber (2) is sealed fluid-tight from the outside, and whereby the capillary membranes of each system are in a fluid connection with their lumens with an inlet device (7) and/or an outlet device (8), and whereby interior chamber (2) has a volume between 0.1 and 5 $cm^3$.

15 Claims, 1 Drawing Sheet

OTHER PUBLICATIONS

R. Pieters et al., "In Vitro Drug Sensitivity of Cells from Children with Leukemia Using the MTT Assay with Improved Culture Conditions", Blood, vol. 76, No. 11, pp. 2327–2336.

Joseph J. Casciari et al., "Growth and Chemotherapeutic Response of Cells in a Hollow–Fiber In Vitro Solid Tumor Model", Journal of the National Cancer Institute, vol. 86, No. 24, pp. 1846–1852, Dec. 21, 1994.

G.J.L. Kaspers et al., "In Vitro Cellular Drug Resistance and Prognosis in Newly Diagnosed Childhood Acute Lymphoblastic Leukemia", Blood, (1997), vol. 90, No. 7, pp. 2723–2729.

K.M. Nicholson et al., "The Influence of Concentration and Time (CxT) on the Sensitivity of DLD–1 Monolayers and Spheroids to Taxol", Ann. Oncology (1996), vol. 7, Supplement 1, Abstract.

* cited by examiner

MEMBRANE MODULE FOR TESTING ACTIVE SUBSTANCES AT CELLS

BACKGROUND OF THE INVENTION

1. Field of the Invention

The invention relates to a membrane module for testing active substances on cells as well as its use.

2. Discussion of Related Art

In the area of cancer research or cancer therapy, for example, it is often necessary by rapid tests to investigate the effect of cytostatics on cancer or tumor cells of a cancer patient to evaluate the possible outcome of chemotherapy. It is therefore necessary to perform an active substance screening to determine the effect of a plurality of active substances in different dosages over time, i.e., with different pharmacokinetics on the cancer cells, and thus, to predict the response of patients to a given chemotherapy with considerable reliability.

Such patient-specific testing of known active substances differs from the active substance tests that are performed in so-called animal models in which the human tumor cells are encapsulated in hollow fiber membrane pieces and then implanted in a recipient animal as proposed, for example, in WO 94/25074 and U.S. Pat. No. 5,676,924. In this method, in contrast to direct implantation of such cells in a receiving animal, encapsulation prevents an immune response of the recipient animal and different tumor cells can be investigated simultaneously per each treatment of the receiving animal with a cytostatic. However, this procedure has limits owing to its naturally poor automation probability and frequently poor transmissibility of the test results to human beings.

Therefore, tests are being conducted to determine patient-specific and tumor-specific responses by means of in-vitro tests. In such tests, the effect of a test substance, for example, an active substance, on the cell cultures is investigated in using cell cultures of the tumor to be investigated. This is known as cell culture assays. In such investigations, standard culture vessels and methods are usually employed which, however, do not allow three-dimensional growth of the cells, i.e., real tumors cannot be simulated. The efficiency, for example, of cytostatics is influenced considerably by the spatial arrangement of the cells and their accessibility. In addition, an adjustment of pharmacokinetics, i.e., the influence of a certain concentration-time curve of the active substance or a combined therapy in which different active substances are to be investigated in succession over time, is not possible, or only with very limited possibility, with the known in-vitro methods.

In German Application 199 10 540.5, filed on the same day, a method for in-vitro testing of active substances using a membrane module is proposed by which the disadvantages of the known in-vitro tests are at least reduced. For example, tumor cells are placed in the cell culture space of the membrane module and membrane systems are used in a cell culture space for supplying a nutrient medium and for oxygenation, supplying cells with oxygen. At least one active substance to be investigated is added to the cell culture space using a specific concentration-time curve, and the cell vitality of the cells located in the cell culture space is monitored simultaneously.

Various membrane modules are known for growing cells. Thus, in DE-A-36 33 891, a device for cultivating animal cells is described by which cells are grown and valuable substances, i.e., products, are to be obtained from the cells. This device contains essentially parallel capillary membranes in a mat-shaped arrangement, whose ends are embedded in cast material and through which the cells are supplied with nutrient materials. In this device, other membranes can be used for improved oxygen supply to the cells. In the finished membrane module, the capillary membranes are essentially parallel to one another and to the housing axis.

U.S. Pat. No. 5,516,691 discloses a module for growing and using metabolic performance to obtain microorganisms, especially cells or bacteria. The module consists of an external housing and at least three independent membrane systems, wherein at least two membrane systems in the form of hollow fiber membranes form a thickly-packed network of layers overlying one another in a crossed pattern. The hollow fiber membranes are embedded at at least one end in cast material and communicate with at least one inlet or an inlet and an outlet. There are microorganisms, especially cells, in the external space between the hollow fiber membranes. The transport of nutrient materials, gases, and metabolic products to or from the cells located in the interior of the module takes place by the various hollow fiber membrane systems.

The membrane module according to U.S. Pat. No. 5,516,691 is preferably used for growing liver cells and is used in an extracorporal liver support system. The important thing here is to use the metabolic performance of the cells. This requires growing as large a number of cells as possible in a membrane module and thus preparing a large module volume for taking up the cells. In U.S. Pat. No. 5,516,691, a test module with the external dimensions 12×12 cm is described, in which 100 layers of hollow fiber membranes are located one on top of the other, and an additional 50 hollow fiber membrane layers are placed vertically from top to bottom to form a thickly packed network with the other layers. The membrane modules described have a complex structure, and are not suitable for active substance screening in which a plurality of membrane modules must be used.

Neither the module design in DE-A-36 33 891 nor the one in U.S. Pat. No. 5,516,691 can be used for testing active substances on cells, especially for active substance screening.

SUMMARY OF THE INVENTION

It is therefore the goal of the present invention to provide a membrane module suitable for testing active substances on cells and especially for screening such active substances. In particular, the present invention tests a plurality of active substances which are also investigated with different concentration/time curves.

This goal is achieved by a membrane module for testing active substances on cells consisting of a housing with an interior chamber bounded by a lid, a bottom, and a side wall and there is a system of first capillary membranes and a system of second capillary membranes, and possibly at least an additional system of capillary membranes inside the interior chamber, wherein each capillary membrane has a first and a second end as well as a lumen fillable with a fluid, and the capillary membranes are arranged in the interior chamber in a layer parallel to the bottom where cell culture space is formed around the capillary membranes in the interior of the housing in the extracapillary space, with the capillary membranes penetrate by at least one of their ends through the side wall of the interior chamber so that, separated by systems, at least one end is embedded in a casting material so the interior chamber is sealed fluid-tight from the outside, and wherein the lumens of the capillary membranes of each system are in a fluid connection with an inlet device and/or an outlet device, with the membrane module comprising the interior having a volume between 0.1 and 5 cm$^3$.

DESCRIPTION OF PREFERRED EMBODIMENTS

Figure 1:
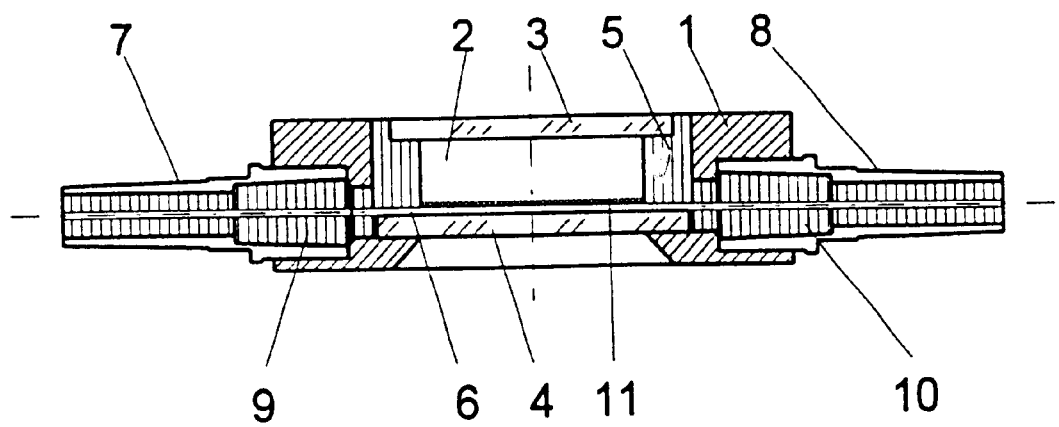
FIG. 1 is a cross section through a membrane module of the invention.

First, by virtue of the design of the membrane module of the invention, it is possible to keep the cells on which the active substances are to be tested under culture conditions to simulate in-vivo conditions as exactly as possible, thus replicating the conditions in the living organism. In addition, the interior volume of the membrane module of the invention is small, comprising between 0.1 and 5 cm$^3$ used for testing the active substances, in particular for active substance screening. Such active substance screening is only possible if only a small amount of cell material is used for the individual active substance test so that, for example, a cancer patient need have only a small number of cells removed in order to test for a plurality of active substances. Thus, for example, a plurality of cytostatics or active substance combinations with different active substance profiles, i.e., with different pharmacokinetics may be tested for suitability for combating cancer, thus an active substance screening may be performed. A plurality of the membrane modules of the invention that can be connected in parallel in a corresponding modular system is used for this purpose. Preferably, the membrane module of the invention is used for testing active substances in cells. The active substances to be tested are those substances whose effect on cells being investigated cannot be predicted well enough before the test or their patient- or tumor-specific effect cannot be predicted. Such active substances are, for example, cytostatics, antibiotics, cytokines, growth factors, or antiviral agents.

The capillary membranes used in the membrane module of the invention can have different external contours, i.e., various external circumferences as viewed in cross section. The capillary membranes can have, for example, a round or circular, triangular, quadrangular, hexagonal, or octagonal shape and they can also be oval, elliptical, three-lobed, four-lobed, etc. The capillary membranes of different systems can also have different external contours. The same applies to the internal cross section of the capillary membranes. Preferably, capillary membranes with essentially circular contours are used.

To avoid dead-space zones in the interior chamber, the interior chamber of the module of the invention, as viewed in the direction perpendicular to at least one capillary membrane layer, preferably has a circular internal cross section. More preferably, the interior has a diameter between 10 and 20 mm. In a more preferred embodiment, the interior chamber has a volume between 0.3 and 3.0 ml.

Preferably, the first capillary membranes continuously supply of nutrient substances and remove metabolic products. In this case, both ends of the first capillary membrane are embedded in a cast material and the lumen of the first capillary membrane is in a fluid connection with both an inlet device and with an outlet device, and can be traversed by the nutrient medium solution in a cross-flow mode. The first capillary membranes must be suitable for supplying a fluid nutrient medium. Preferably, this is a membrane that allows continuous material transport through the membrane wall using diffusive or convective transport mechanisms. Depending on the requirement, i.e., depending on whether diffusive or convective transport of the nutrient medium through the membrane is necessary, nanofiltration or ultrafiltration membranes or microfiltration membranes are used.

In another preferred embodiment of the membrane module of the invention, the first capillary membranes are in a fluid connection by their lumen only with an inlet device but not with an outlet device. The first capillary membranes serve in this case only for supplying a nutrient medium solution, which then flows through the first capillary membranes in a dead-end mode but does not carry away metabolic products. For example, both ends of the first capillary membranes can be embedded in the same casting material, wherein the first capillary membranes are then positioned, for example, as U-shaped loops in the interior chamber.

With such an arrangement of the first capillary membranes, a system of third capillary membranes is located inside the membrane module of the invention, by which the metabolic products of the cells can be carried away. Preferably, the third capillary membranes are likewise membranes through which flow takes place in the dead-end mode, whose lumen in this case is in a fluid connection only with an outlet device, but not with an inlet device. In such an embodiment of the membrane module of the invention, the walls of the first and the third capillary membranes preferably can be traversed convectively, wherein the first and third capillary membranes are preferably microfiltration membranes. When used, a fluid stream containing the nutrient medium flows through the first capillary membranes into the extracapillary cell culture chamber and flows through the latter, wherein nutrient substances are given off to the cells and metabolic products are given off to the fluid stream. Then the fluid stream, enriched with the metabolic products, is removed from the cell culture space by the third capillary membranes. For this purpose, the membrane module of the invention is preferably made pressure-tight to an internal pressure of 500 mbar in the interior chamber.

The second capillary membranes preferably are membranes suitable for conducting a gaseous material into the interior chamber. Thus, they are membranes for the gas transfer of oxygen, for example, into the modular interior or of carbon dioxide from the module interior, i.e., they are oxygenation membranes. For the preferred case where both the addition of oxygen and the removal of carbon dioxide take place by means of the second capillary membranes, the second capillary membranes are in a fluid connection both with an inlet device and also with an outlet device. However, it is also possible that only oxygen can be added by means of the second capillary membranes and carbon dioxide, for example, can be carried away with the removal of metabolic products by the first or the third capillary membranes. In this case, the second capillary membranes are in a fluid connection by their lumen only with an inlet device and flow through them is in a dead-end mode.

In another preferred embodiment of the membrane module of the invention, the lumens of the first and second capillary membranes are connected both with an inlet device and with an outlet device. Thus, the flow can take place through them in a cross-flow mode. In this case, the first and second ends of the capillary membranes of a system pass through the side wall of the interior chamber on opposite sides of the interior. Naturally, it is also possible for the throughput locations of the ends of the capillary membranes of a system to be located at an angle to one another, for example, at a right angle.

The module of the invention comprises supplying an active substance to the cell culture chamber. In one preferred embodiment, the supplying consists of the first capillary membranes. In this case, the active substance to be investigated is added to the nutrient medium flow when this membrane module is used and enters the cell culture chamber with the nutrient medium flow. Concentration-time profiles of the active substance are then influenced by the permeability of the first capillary membranes.

In another preferred embodiment, the supplying for an active substance consists of at least one inlet to the interior, for example, in the form of at least one bore through the side wall, to which an inlet device or a metering unit for the active substance is connected to the exterior of the module. The inlet can also have a septum, a separating wall between the interior and the outer environment of the module which is part of the lid, the bottom, or the side wall, and which, for example, can be penetrated by capillaries for dispensing the active substance and which closes fluid-tight after the capillaries are removed. Such a septum can also be advantageously used to supply the cell culture to the interior or to remove samples from the interior. The cell culture can be added to the interior chamber through the lid, which is made removable for this purpose. Likewise, the cell culture chamber can be evacuated as necessary, for example, by means of a capillary through the septum or likewise through a removable lid. Evacuation however can also take place through a hydrophobic porous membrane, for example, which is embedded for example in the inside wall and connects the interior with the exterior of the module.

According to another advantageous embodiment, the supplying an active substance can be another system of capillary membranes through which the active substance to be tested is supplied to the interior.

Another system of capillary membranes can be contained in the membrane module of the invention so that samples can be removed from the cell culture chamber, for example.

For uniform nutrient supply and removal, uniform oxygenation and, in the case of the active substances coming in through one of the membrane systems to guarantee a uniform active substance supply, the capillary membranes within a layer are distributed uniformly over the interior cross section of the interior chamber as viewed perpendicularly to that layer. The preferred maximum horizontal distance between adjacent capillary membranes within a layer is in the range between 50 and 500 $\mu$m. It is also advantageous if the capillary membranes of different systems are in a cross-wise arrangement as viewed perpendicularly to the layers in the viewing direction. This can be accomplished, for example, by having the first and second capillary membranes woven together to form a fabric. In a preferred embodiment, the capillary membranes are arranged separated by systems in at least one layer respectively, wherein the layers are arranged on top of one another so that the capillary membranes of different systems cross as viewed perpendicularly to the layers.

Preferably, the membrane module of the invention contains 2 to 15 layers of each system of capillary membranes. The total number of capillary membrane layers in the interior is preferably 2 to 20.

Because of the sedimentation behavior of the cells added to the cell culture chamber when using the membrane module of the invention, preferably several layers of capillaries are located in the interior which are distributed asymmetrically, with a denser sequence near the bottom over the height of the interior between the lid and the bottom.

Membrane modules with interior volumes like those of the membrane modules of the invention are connected with a number of capillary membranes that is small by comparison to larger volume modules wherein the capillary membranes preferably are located in the interior chamber in layers with a uniform distribution of the capillary membranes over the interior cross section. In such membrane modules, embedding the ends of the capillary membranes as well as connecting them with an inlet and/or outlet device is often difficult. In a preferred embodiment of the membrane module of the invention, the ends of the capillary membranes of the individual systems are merged into bundles and in a tubular end piece, for example, in the form of a tube opening embedded in a casting material. The tubular end pieces with the capillary membranes embedded therein which simultaneously constitute the inlet device or outlet device, can be glued fluid-tight with a suitable adhesive in a simple fashion in the side wall of the interior of the membrane module of the invention and connected by their free ends to the supply line or drain line.

When a membrane module of the invention is used, it is frequently necessary visually to observe the cells in the cell culture chamber, for example, to view them under the microscope. For this purpose the lid and the bottom are parallel in a preferred membrane module and each made in one piece from a transparent material each.

Preferably, the membrane module according to the invention is provided at least partially with a heating foil in order to make it possible to control the internal temperature, for example, at 37° C. Such temperature control is also possible using a heat exchanger system located in the interior chamber, for example, in the form of a system of capillaries similar to the systems of capillary membranes located in the interior chamber, with the capillaries having fluid-tight walls and a tempering fluid flowing through them.

The membrane module of the invention is suitable both for active substance testing on suspension cells, i.e., on cells present in suspensions, as well as cells that require adhesion. Cells that require adhesion can adhere to the surfaces inside the membrane module such as the side wall, lid, or bottom, for example, or also in the capillary membranes present in the interior. However, it can happen that when the cells adhere to the capillary membrane surfaces the capillary membranes are no longer completely available for unimpeded material transport. In a preferred embodiment, the membrane module according to the invention therefore contains an internal cell immobilizer, with these means consisting especially favorably of individual textile fibers, cloth, or knit fabric. Especially good experience has been had with cell immobilizers comprising polyester. Such means are described for example in DE-A-36 33 891.

For applications in which suspension cells are used, the membrane module of the invention contains layer-shaped carriers, in a preferred embodiment, which are added over the height of the interior chamber and distributed between the layers of the capillary membranes. Also, in cases in which the suspension cells have a strong tendency to sediment out, these layer-shaped carriers have a better distribution of the suspension cells over the height of the cell culture space. The carrier materials, for example, can be in the form of a microporous flat membrane or in the form of a fleece, wherein the pore sizes of the flat membranes or the fleece are so dimensioned that the suspension cells are at least considerably held back by such a flat membrane or by such a fleece. By using such carrier substances, the suspension cells are held in different layers. The membrane module of the invention in these cases advantageously permits the addition of suspension cells, with the cells at various positions over the height of the interior chamber, for example, by a corresponding number of septa distributed over the height in the side wall. The same is also true for the addition of active substances.

Because of the design of the invention, the interior of the membrane module of the invention, very uniform conditions prevail, for example, in nutrient medium concentration, the concentrations of individual gas components, and temperature. Therefore, one preferred embodiment of the module of the invention comprises at least one sensor for monitoring the conditions in the interior of the module, and more preferably at least a microsensor, a sensor which is adapted in terms of its dimensions to the small dimensions of the membrane module according to the invention, wherein as far as the position of such sensors, no special requirements are imposed because of the uniform conditions in the interior. Such microsensors can measure online the pH value, oxygen partial pressure, glucose concentration, lactate concentration, pressure and/or temperature in the interior, and no disturbing influence of the sensor or the sensors on the cell culture located in the cell culture space is caused by miniaturization.

The invention will be described below with reference to the figures. In a simplified schematic representation:

In FIG. 1, on an enlarged scale, a membrane module of the invention is shown, which has a multipartite housing 1 with an interior chamber 2 to receive a cell culture. The interior chamber 2 is limited by a lid 3, a bottom 4 parallel to the lid, and a side wall 5, and the viewing direction perpendicular to the lid or the bottom has a circular interior cross section. Lid 3 and bottom 4 consist of transparent material in order to permit observation of the cells in the interior. Side wall 5 consists in the present example of a hardened casting material in which the capillary membranes which are in the vicinity of the bottom are simultaneously embedded so that a fluid-tight seal between the interior chamber 2 and the exterior of the housing results.

In the interior chamber, the first capillary membranes 6 are located in the form of a single layer which have flow through them in a cross-flow mode and whose ends emerge on opposite sides through the side wall of the interior from the interior and are embedded in inlet and outlet tube openings 7, 8 in a casting material 9, 10. The membrane module according to FIG. 1 contains a layer of second capillary membranes 11 which, in the drawing shown, run perpendicularly to the plane of the drawing.

Figure 2:
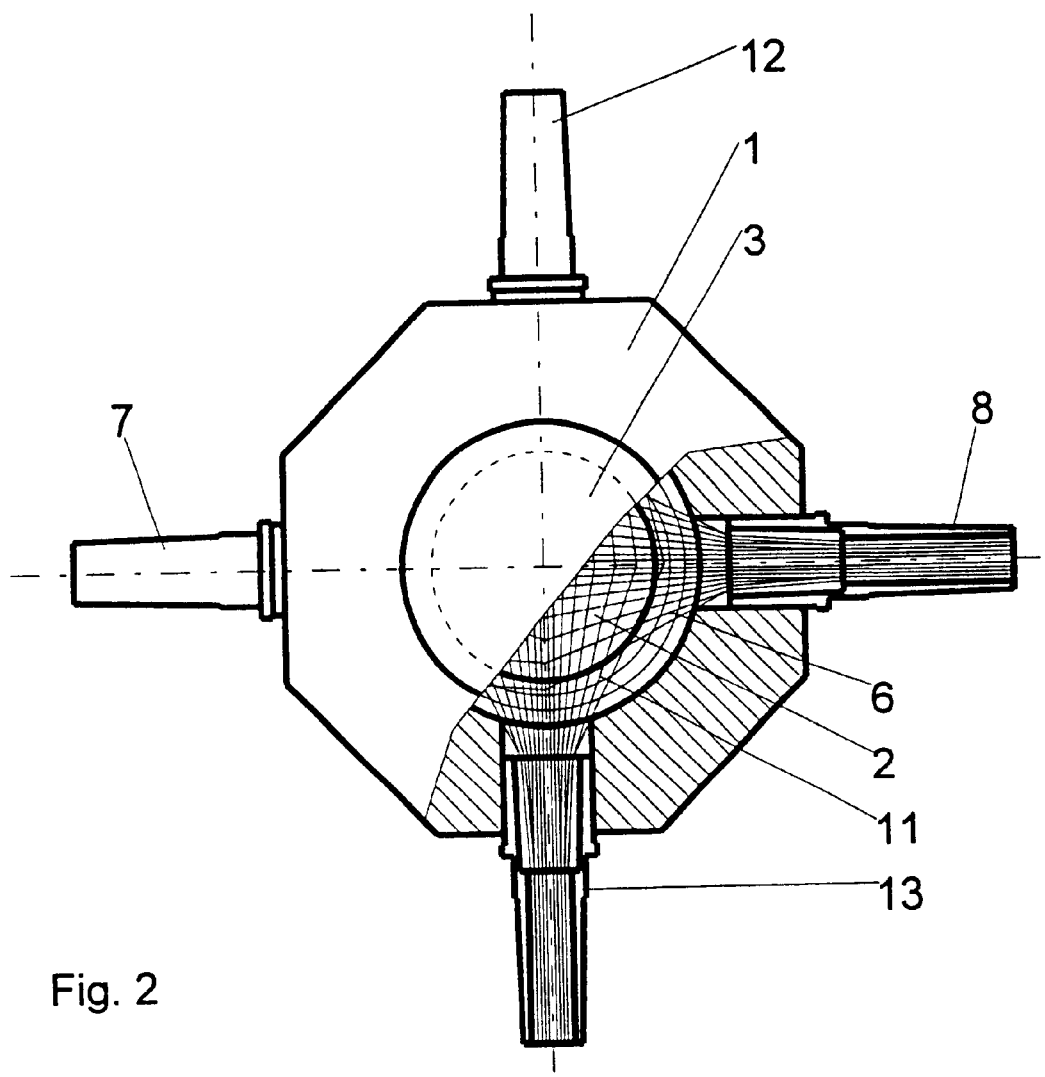
FIG. 2 is a top view of the membrane module of the invention shown in FIG. 1 with partial breakout showing the distribution of the capillary membranes in the interior.

FIG. 2 shows the membrane module in FIG. 1 in a top view with a partial breakout in order to make the arrangement of the capillary membranes in the interior of the module clear. Interior chamber 2 is surrounded by housing 1 and covered by a circular lid 3. In interior chamber 2 the first and the second capillary membranes 6, 11 are distributed uniformly over the interior cross section of the internal chamber 2. The first capillary membranes 6 in this view run from right to left, wherein in the interior, they are uniformly distributed over the internal cross section and their ends are collected into bundles in inlet and outlet tube openings 7, 8 and embedded therein. The second capillary membranes 11 in this view run from top to bottom and are also uniformly distributed over the internal cross section in the interior, collected into bundles at their ends and embedded in inlet and outlet tube openings 12, 13. The first and second capillary membranes 6, 11 cross each other in interior chamber 2.

We claim:

1. A membrane module for testing active substances in cells, comprising a housing with an interior chamber, closed by a lid, a bottom, and a side wall, and a system of first capillary membranes and a system of second capillary membranes arranged in the interior chamber and optionally additional systems of capillary membranes, wherein each capillary membrane has a first and a second end as well as a lumen through which a fluid can be transported, wherein the capillary membranes in the interior chamber are located in a flat layer parallel to the bottom, and in the interior chamber of the housing in an extracapillary space around the capillary membranes a cell culture chamber is formed, wherein the capillary membranes have ends and at least one of the ends penetrates through the side wall of the interior chamber, and separated by systems, the at least one of the ends is embedded in a casting material so the interior chamber is sealed off fluid-tight from outside, and wherein the lumens of the capillary membranes of each system with their lumens have a fluid connection with an inlet device, an outlet device or both, and wherein the interior chamber has a volume between 0.1 and 5 $cm^3$.

2. The membrane module according to claim 1, wherein the interior chamber, viewed in a direction perpendicular to at least one layer, has a circular interior cross section.

3. The membrane module according to claim 1, wherein the interior chamber has a diameter between 10 and 20 mm.

4. The membrane module according to claim 1, wherein the lid and the bottom are parallel to one another, and are each made in one piece from transparent material.

5. The membrane module according to claim 1, wherein the capillary membranes, viewed in a direction perpendicular to at least one layer, are distributed within a layer uniformly over an internal cross section of the interior chamber.

6. The membrane module according to claim 1, wherein the capillary membranes of different systems are placed in a cross-wise arrangement when viewed perpendicularly toward at least one layer.

7. The membrane module according to claim 1, wherein the membrane module comprises means for supplying an active substance to the interior chamber.

8. The membrane module according to claim 7, wherein the means for supplying the active substance to the interior chamber consists of at least one inlet in the side wall.

9. The membrane module according to claim 7, wherein the means for supplying the active substance to the interior chamber comprises of another system of capillary membranes.

10. The membrane module according to claim 1, wherein the ends of the capillary membranes of the individual systems are collected into bundles and are embedded in a tubular end piece.

11. The membrane module according to claim 1, wherein a plurality of layers of capillary membranes are located in the interior chamber, which are distributed over the height of the interior chamber, and between the lid and the bottom asymmetrically with a denser sequence in the vicinity of the bottom.

12. The membrane module according to claim 1, wherein a cell immobilizer is located in the interior chamber.

13. The membrane module according to claim 12, wherein the cell immobilizer comprises textile individual fibers, fabrics, or knits.

14. The membrane module according to claim 1, wherein the first capillary membranes are microfiltration membranes suitable for transporting a fluid nutrient medium to the interior space, and the second capillary membranes are membranes suitable for supplying a gaseous material to the interior.

15. A process for testing comprising introducing the active substances through the membrane module of claim 1, and monitoring the conditions of the interior of the membrane module.

* * * * *